(12) United States Patent
Lombardi et al.

(10) Patent No.: US 6,740,115 B2
(45) Date of Patent: May 25, 2004

(54) COVERED STENT WITH ENCAPSULATED ENDS

(75) Inventors: Sylvie Lombardi, Karlsruhe (DE); Guido Koch, Karlsruhe (DE); Richard Layne, E. Palo Alto, CA (US); Tarun Edwin, Chandler, AZ (US); Wolfgang Supper, Karlsruhe (DE); Walter Gamer, Bruchsal (DE); Thomas Kirchhoff, Walsbachtal (DE)

(73) Assignee: C. R. Bard, Inc., Murray Hills, NJ (US)

( * ) Notice: Subject to any disclaimer, the term of this patent is extended or adjusted under 35 U.S.C. 154(b) by 0 days.

(21) Appl. No.: 10/412,138

(22) Filed: Apr. 11, 2003

(65) Prior Publication Data

US 2003/0191519 A1 Oct. 9, 2003

Related U.S. Application Data

(63) Continuation of application No. 09/430,154, filed on Oct. 29, 1999, now Pat. No. 6,579,314, which is a continuation-in-part of application No. 08/401,871, filed on Mar. 10, 1995, now Pat. No. 6,124,523.
(60) Provisional application No. 60/118,269, filed on Feb. 2, 1999.

(51) Int. Cl.[7] .................................. A61F 2/06
(52) U.S. Cl. ..................... 623/1.44; 623/1.15; 623/1.31
(58) Field of Search ............................. 606/1, 108, 151, 606/191–200; 623/1.1–1.54

(56) References Cited

U.S. PATENT DOCUMENTS

| | | |
|---|---|---|
| 4,776,337 A | 10/1988 | Palmaz |
| 5,122,154 A | 6/1992 | Rhodes |
| 5,139,480 A | 8/1992 | Hickle et al. |
| 5,158,548 A | 10/1992 | Lau et al. |
| 5,211,658 A | 5/1993 | Clouse |
| 5,236,447 A | 8/1993 | Kubo et al. |
| 5,242,399 A | 9/1993 | Lau et al. |
| 5,258,027 A | 11/1993 | Berghaus |
| 5,282,823 A | 2/1994 | Schwartz et al. |
| 5,344,426 A | 9/1994 | Lau et al. |
| 5,354,309 A | 10/1994 | Schnepp-Pesch et al. |
| 5,383,928 A | 1/1995 | Scott et al. |
| 5,389,106 A | 2/1995 | Tower |
| 5,395,390 A | 3/1995 | Simon et al. |
| 5,421,955 A | 6/1995 | Lau et al. |
| 5,437,083 A | 8/1995 | Williams et al. |
| 5,443,496 A | 8/1995 | Schwartz et al. |
| 5,458,615 A | 10/1995 | Klemm et al. |
| 5,474,563 A | 12/1995 | Myler et al. |
| 5,507,767 A | 4/1996 | Maeda et al. |
| 5,507,768 A | 4/1996 | Lau et al. |

(List continued on next page.)

FOREIGN PATENT DOCUMENTS

| | | |
|---|---|---|
| EP | 0 603 959 A1 | 6/1994 |
| FR | 2 671 482 A1 | 7/1992 |
| WO | WO 94/24961 | 11/1994 |
| WO | WO 97/21403 | 6/1997 |
| WO | WO 98/26731 | 6/1998 |
| WO | PCT/US 00/02885 | 7/2000 |

*Primary Examiner*—Glenn K. Dawson
(74) *Attorney, Agent, or Firm*—Morrison & Foerster LLP

(57) ABSTRACT

A flexible covered stent includes a stent covered on a first surface by a first layer of biocompatible material and on a second surface by a second layer of biocompatible material, the first and second layers of biocompatible material being bonded to one another through a wall in the stent. The first layer of biocompatible material is longer than the second layer of biocompatible material such that at least a portion of the second surface of the stent is left uncovered, imparting flexibility to the stent. A mid portion of the second surface of the stent can be left uncovered to impart flexibility to the stent similar to that enjoyed by a bare stent.

7 Claims, 7 Drawing Sheets

U.S. PATENT DOCUMENTS

| | | |
|---|---|---|
| 5,514,154 A | 5/1996 | Lau et al. |
| 5,522,881 A | 6/1996 | Lentz |
| 5,527,353 A | 6/1996 | Schmitt |
| 5,527,355 A | 6/1996 | Ahn |
| 5,546,646 A | 8/1996 | Williams et al. |
| 5,549,663 A | 8/1996 | Cottone, Jr. |
| 5,554,181 A | 9/1996 | Das |
| 5,569,295 A | 10/1996 | Lam |
| 5,591,223 A | 1/1997 | Lock et al. |
| 5,593,417 A | 1/1997 | Rhodes |
| 5,603,721 A | 2/1997 | Lau et al. |
| 5,632,840 A | 5/1997 | Campbell |
| 5,645,559 A | 7/1997 | Hachtman et al. |
| 5,649,950 A | 7/1997 | Bourne et al. |
| 5,649,977 A | 7/1997 | Campbell |
| 5,653,727 A | 8/1997 | Wiktor |
| 5,653,747 A | 8/1997 | Dereume |
| 5,667,523 A | 9/1997 | Bynon et al. |
| 5,683,453 A | 11/1997 | Palmaz |
| 5,693,085 A | 12/1997 | Buirge et al. |
| 5,700,286 A | 12/1997 | Taraglia et al. |
| 5,713,949 A | 2/1998 | Jayaraman |
| 5,718,973 A | 2/1998 | Lewis et al. |
| 5,723,003 A | 3/1998 | Winston et al. |
| 5,728,131 A | 3/1998 | Frantzen et al. |
| 5,728,158 A | 3/1998 | Lau et al. |
| 5,735,892 A | 4/1998 | Myers et al. |
| 5,735,893 A | 4/1998 | Lau et al. |
| 5,738,674 A | 4/1998 | Williams et al. |
| 5,749,880 A | 5/1998 | Banas et al. |
| 5,755,770 A | 5/1998 | Ravenscroft |
| 5,755,774 A | 5/1998 | Pinchuk |
| 5,755,781 A * | 5/1998 | Jayaraman .................. 623/1.1 |
| 5,766,238 A | 6/1998 | Lau et al. |
| 5,769,884 A | 6/1998 | Solovay |
| 5,810,870 A | 9/1998 | Myers et al. |
| 5,824,037 A | 10/1998 | Fogarty et al. |
| 5,824,043 A | 10/1998 | Cottone, Jr. |
| 5,824,046 A | 10/1998 | Smith et al. |
| 5,824,054 A | 10/1998 | Khosravi et al. |
| 5,843,161 A | 12/1998 | Solovay |
| 5,843,166 A | 12/1998 | Lentz et al. |
| 5,849,037 A | 12/1998 | Frid |
| 5,851,232 A | 12/1998 | Lois |
| 5,876,448 A | 3/1999 | Thompson et al. |
| 5,928,279 A | 7/1999 | Shannon et al. |
| 6,042,605 A | 3/2000 | Martin et al. |
| 6,379,379 B1 * | 4/2002 | Wang ........................ 623/1.15 |
| 6,398,803 B1 * | 6/2002 | Layne et al. ................ 623/1.13 |
| 6,579,314 B1 * | 6/2003 | Lombardi et al. .......... 623/1.44 |

* cited by examiner

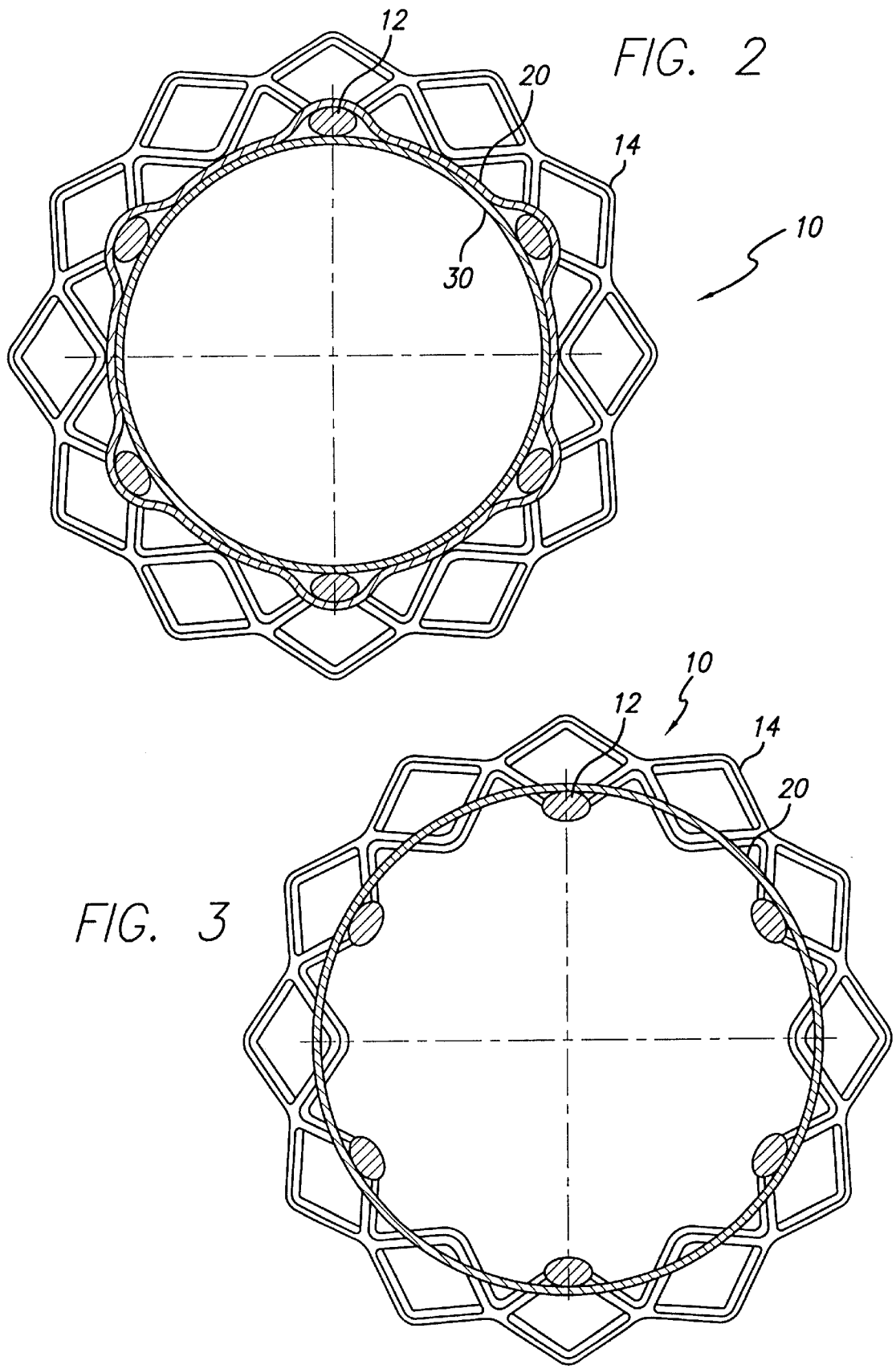

COVERED STENT WITH ENCAPSULATED ENDS

CROSS-REFERENCE TO RELATED APPLICATIONS

This application is a continuation of application Ser. No. 09/430,154, filed Oct. 29, 1999, now U.S. Pat. No. 6,579,314, which claims the benefit of provisional application Ser. No. 60/118,269, filed Feb. 2, 1999, and which is a continuation-in-part of application Ser. No. 08/401,871, filed Mar. 10, 1995, now U.S. Pat. No. 6,124,523. The entirety of each of these applications is expressly incorporated by reference as if fully set forth herein.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

Stents and similar endoluminal devices are currently used by medical practitioners to treat tubular body vessels or ducts that become so narrowed (stenosed) that flow of blood or other biological fluids is restricted. Such narrowing (stenosis) occurs, for example, as a result of the disease process known as arteriosclerosis. While stents are most often used to "prop open" blood vessels, they can also be used to reinforce collapsed or narrowed tubular structures in the respiratory system, the reproductive system, bile or liver ducts or any other tubular body structure. However, stents are generally mesh-like so that endothelial and other tissues can grow through the openings resulting in restenosis of the vessel.

Polytetrafluoroethylene (PTFE) has proven unusually advantageous as a material from which to fabricate blood vessel grafts or prostheses, tubular structures that can be used to replace damaged or diseased vessels. This is partially because PTFE is extremely biocompatible causing little or no immunogenic reaction when placed within the human body. This is also because in its preferred form, expanded PTFE (ePTFE), the material is light and porous and is readily colonized by living cells so that it becomes a permanent part of the body. The process of making ePTFE of vascular graft grade is well known to one of ordinary skill in the art. Suffice it to say that the critical step in this process is the expansion of PTFE into ePTFE. This expansion represents a controlled longitudinal stretching in which the PTFE is stretched to several hundred percent of its original length.

Apart from use of stents within the circulatory system, stents have proven to be useful in dealing with various types of liver disease in which the main bile duct becomes scarred or otherwise blocked by neoplastic growths, etc. Such blockage prevents or retards flow of bile into the intestine and can result in serious liver damage. Because the liver is responsible for removing toxins from the blood stream, is the primary site for the breakdown of circulating blood cells and is also the source of vital blood clotting factors, blockage of the bile duct can lead to fatal complications. A popular type of stent for use in the biliary duct has been one formed from a shape memory alloy (e.g., nitinol) partially because such stents can be reduced to a very low profile and remain flexible for insertion through the sharp bend of the bile duct while being self-expandable and capable of exerting a constant radial force to the duct wall.

Cellular infiltration through stents can be prevented by enclosing the stents with ePTFE. Early attempts to produce a stent covered by ePTFE focused around use of adhesives or physical attachment such as suturing. However, such methods are far from ideal and suturing, in particular, is very labor intensive. More recently methods have been developed for encapsulating a stent between two tubular ePTFE members whereby the ePTFE of one-member touches and bonds with the ePTFE of the other member through the mesh opening in the stent. However, such a monolithically encapsulated stent may tend to be rather inflexible. Therefore, there is a need for a stent covered to prevent cellular infiltration and yet still flexible to ensure ease of insertion and deployment and to accommodate extreme anatomical curves.

BRIEF SUMMARY OF THE INVENTION

The present invention is directed to covered stents wherein flexibility of the stent is retained, despite the use of encapsulation techniques. Encapsulation refers to the lamination of a stent between an inner and an outer layer of a plastic material. Compared to a fully encapsulated stent enhanced flexibility can be achieved by encapsulating limited regions of the stent, while leaving a significant portion of the stent—usually a middle portion—covered by a single layer of the plastic material. In this way the limited encapsulation fixes the plastic covering onto the stent with no need for sutures or similar labor intensive mechanical attachments.

It is an object of this invention to provide a stent device that has improved flexibility compared to a fully encapsulated stent, yet maintains its impermeability to infiltrating tissues.

It is yet another object of this invention to provide a stent device that shows minimal profile when loaded into insertion systems and can be deployed using forces that are reduced compared to those used with fully encapsulated designs.

These and additional objects are accomplished by embedding or encapsulating only portions of the stent between two layers of biocompatible material. This is accomplished by covering either the luminal or abluminal surface of the stent with a layer of biocompatible material, preferably ePTFE, while also covering limited sections of the opposite surface of the stent with the biocompatible material, thereby fully encapsulating only the limited sections. A preferred design fully encapsulates only the end regions of the device. By leaving a middle region of the stent unencapsulated, the stent is free to flex much like a bare stent, increasing overall flexibility and reducing the necessary loading and deployment forces.

In the present invention, a stent is partially encapsulated using the configuration mentioned above. One means of accomplishing this configuration is to place rings (radial strips) of ePTFE on a mandrel at positions corresponding to each end of the stent. The stent is then placed over the mandrel and the rings in registration with the ends of the stent. Finally, the stent (supported by the mandrel) is covered on its abluminal (outside) surface by a tubular ePTFE graft. The resulting structure is then subjected to heat and pressure so that the regions containing ePTFE on both surfaces become laminated or fused together (e.g., a bond is formed). This yields a stent with substantially its entire abluminal surface covered by ePTFE. Regions near the ends of the stent are fully encapsulated (e.g., these regions are covered by ePTFE on their luminal surfaces as well). The fully encapsulated area serves to attach the abluminal covering to the stent.

A more complete understanding of the partial encapsulation of stents will be afforded to those skilled in the art, as well as a realization of additional advantages and objects thereof, by a consideration of the following detailed description of the preferred embodiment. Reference will be made to the appended sheets of drawings, which will first be described briefly.

BRIEF DESCRIPTION OF THE DRAWINGS

FIG. 2 is a cross-sectional view along the line 2—2.

FIG. 3 is a cross-sectional view along the line 3—3.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention.

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
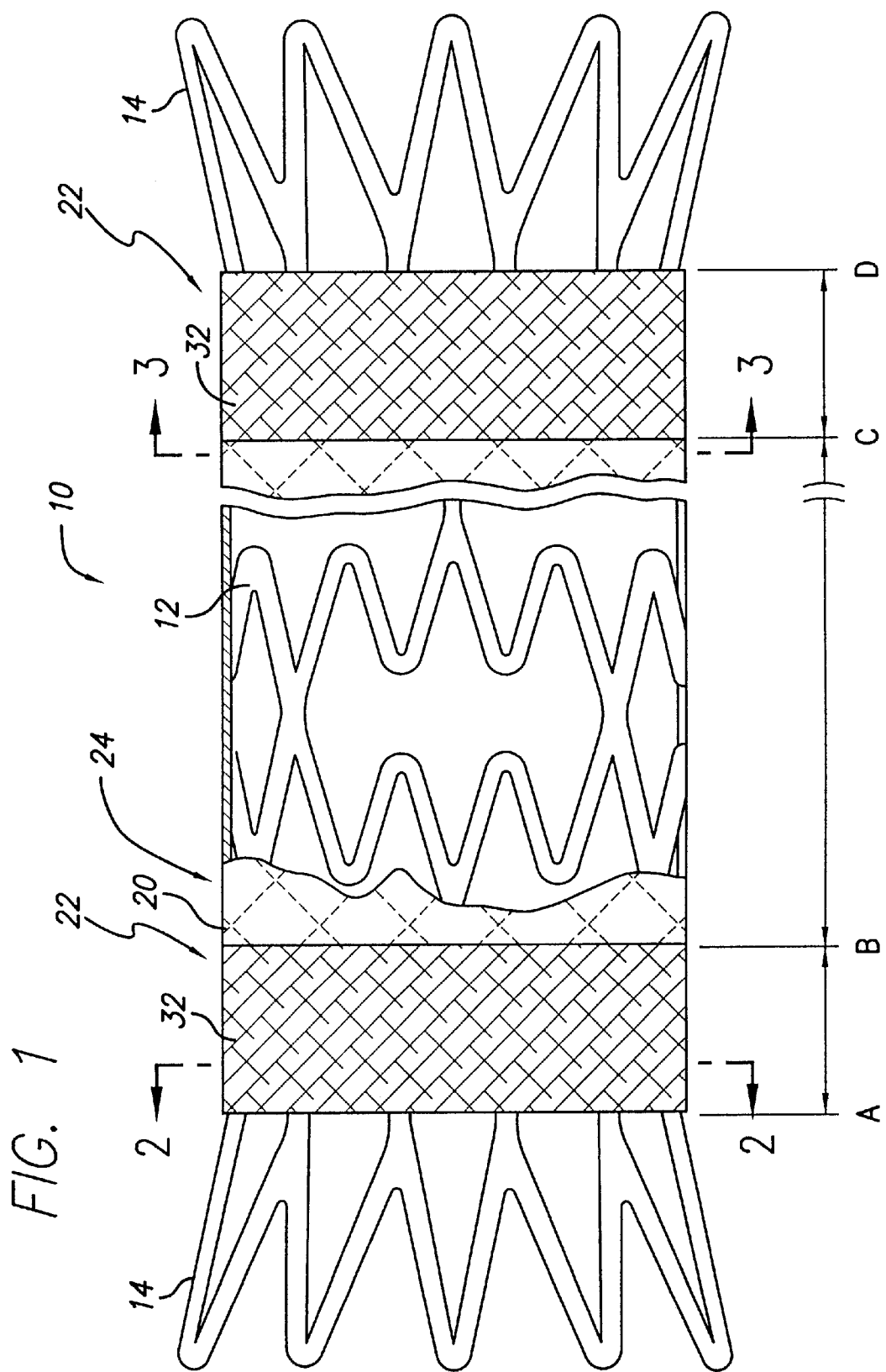
FIG. 1 is a perspective view of the preferred embodiment of the present invention.

The present invention satisfies the need for a covered stent device that is virtually as flexible as an uncovered stent. This is accomplished by covering a stent on a first surface while limited regions are covered on the opposite surface to ensure fixation of the first surface covering. Referring now to the drawings, FIG. 1 illustrates a preferred embodiment of the present invention. A partially encapsulated stent-graft 10 is created by covering the abluminal surface of a stent 12 with a biocompatible barrier material that is able to seal fistulae and aneurysms and prevent or reduce tissue ingrowth from neointimal hyperplasia or tumor growth. In the preferred embodiment, the material used for this purpose is a tubular layer of expanded polytetrafluoroethylene (ePTFE) 20. The preferred ePTFE is one optimized for bond strength as described in U.S. Pat. No. 5,749,880. The stent 12 in the preferred embodiment is a shape memory alloy stent having geometry enhancing the stent's flexibility, although stents of a variety of designs are usable with the current invention because the inventive configuration minimizes the effect of the covering on stent flexibility. Also, the stent 12 can be made out of any type of material besides shape memory alloy.

It will be apparent to those of skill in the art that at a covering over at least one of the surfaces (luminal or abluminal) of the stent is necessary to prevent tissue ingrowth. Furthermore, the covering must be bonded to the stent to prevent it from coming detached and perhaps forming a blockage in the vessel. Although ePTFE has numerous favorable properties, it is relatively difficult to attach it to a stent. Mechanical fasteners such as sutures have the disadvantage of interrupting the integrity of the ePTFE sheet so that leaking can occur. Although ePTFE does not adhere well to a stent, it can be made to bond to itself. Therefore, one effective method of affixing the ePTFE cover is to place ePTFE covers in contact with both the abluminal and luminal surfaces of the stent so that one ePTFE covering can bond to the other where the ePTFE coverings touch through the openings in the stent. The drawback with this approach is that the structural members of the stent are tightly surrounded and held by ePTFE. When the stent bends or expands, the stent structural members must move relative to each other. This movement is resisted by the tightly adhering ePTFE (or other covering material).

In the present invention movement of the stent members relative to each other is facilitated by limiting the region of the stent in which the structural members are surrounded (encapsulated) by ePTFE. In a preferred embodiment the regions of encapsulation, which ensure attachment of the covering to the stent, are limited to areas near the ends of the device. For a relatively short device these end-encapsulated regions are more than adequate to afford attachment of the covering. If necessary one or more additional regions of encapsulation could be added along the length of the device if it is found necessary for stability of the covering. Clearly, the greater the percentage of length of the device that is fully encapsulated, the more the flexibility of the overall structure will be impeded.

An additional advantage of the limited encapsulation of the present invention is the possibility of enhanced healing. It is known that living cells will infiltrate sufficiently porous ePTFE and that microcapillaries may form within and across the ePTFE wall so that a living intima is formed along the luminal surface. Where two layers of ePTFE surround the stent, it may be significantly more difficult for cellular infiltration across the wall to occur. Although the figures show the continuous covering placed on the abluminal surface of the device, the present invention also lends itself to placement of the continuous covering on the luminal surface. The configuration choice may depend on the precise application of the device. In some applications, for example large vessels having a high rate of blood flow placing the covering on the luminal surface may result in advantageous lamellar flow of the blood (ie., blood flow without significant turbulence). There is some evidence that contact of the blood with a metal stent may result in local, limited thrombosis. While this may be detrimental, there is also some evidence that such limited thrombosis results in enhanced healing. An advantage of using a full luminal covering could be improved anchoring of the device within the duct or vessel afforded by interactions between the bare abluminal stent and the duct or vessel wall. Therefore, the optimal configuration will have to be empirically determined in many cases.

In the illustrated design (FIG. 1) the extremities 14 of the stent 12 are left completely uncovered and flare outward to facilitate anchoring of the stent within the vessel following expansion of the stent in situ. It will be apparent that this flared region is a feature of this particular embodiment and is not a required element of the instant invention. The luminal surface of the stent 12 is covered at ends 22 defined between points A and B and points C and D in FIG. 1, but is left uncovered in mid-section 24 defined between points B and C. By leaving the mid-section 24 uncovered, the stent has increased flexibility as well as reduced profile when compressed. The material used to cover the ends 22 on the luminal surface of stent 12 is generally the same material that is used to cover the abluminal surface, and in FIG. 1 this material is ePTFE 30 (see FIG. 2), though any other suitable biocompatible material could be used in the present invention.

Again, it is important to note that while the continuous tubular layer of ePTFE 20 is shown on the abluminal surface of FIG. 1, it is possible, and advantageous in some cases, to place a tubular layer of ePTFE on the luminal surface, while placing limited rings of ePTFE only on the abluminal surfaces at the ends of the device. Distances A–B and C–D in FIG. 1 can be lesser or greater, depending on the need for flexibility in the particular application. Moreover, there can be any number of encapsulated region(s) and these region(s) can be located in different areas of the stent. Also, while the preferred embodiments use encapsulated regions that extend completely around a circumference of the device (e.g., rings of material) as indicated by region 32 in FIG. 1, there is no reason that discontinuous regions of encapsulation cannot be used. Attaching discrete pieces or strips of ePTFE to a mandrel before the stent is placed on the mandrel can be used to form such discontinuous regions. The size, shape and pattern formed by regions 32 can be selected to enhance flexibility, etc. This allows different regions of the device to exhibit different properties of flexibility, etc.

Once the appropriate ePTFE covering is placed onto the luminal and abluminal surfaces, the ends 22 of the stent graft 10 are encapsulated by connecting or bonding the luminal covering to the abluminal covering. Encapsulation can be accomplished by a number of methods including sintering (i.e., heating), suturing, ultrasonically welding, stapling and adhesive bonding. In the preferred embodiment, the stent-graft 10 is subjected to heat and pressure to laminate (bond) the tubular ePTFE layer 20 on the abluminal surface to the two rings of ePTFE 30 on the luminal surface.

Figure 7:
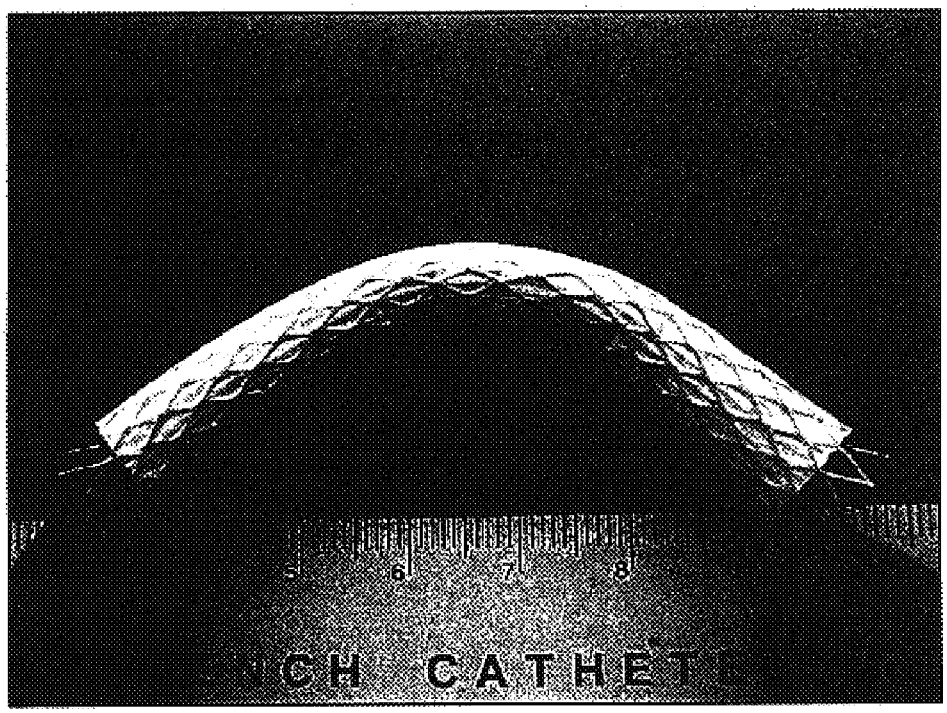
FIG. 7 is a picture of a fully encapsulated stent being tested for flexibility.
Figure 8:
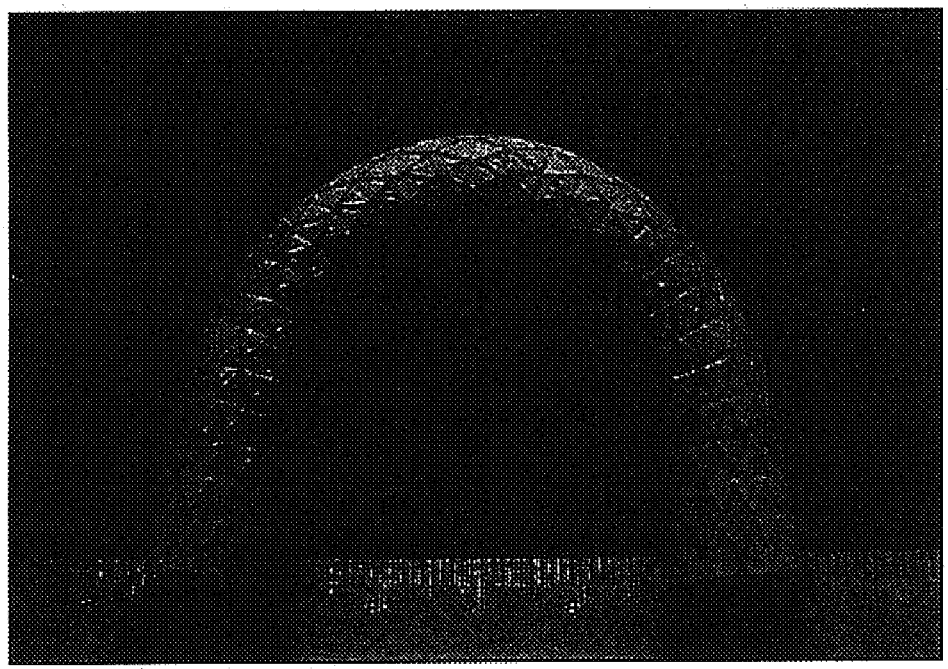
FIG. 8 is a picture of the covered stent of the present invention being tested for flexibility in the same manner as FIG. 7.

FIGS. 2 and 3 illustrate cross-sections of FIG. 1. A cross-section of stent-graft 10 is taken along line 2—2, through an end 22 of the device 10 in FIG. 2 and along line 3—3, through the mid-section 24 in FIG. 3. These two cross-sections are shown to illustrate the additional layer of ePTFE 30 that is present on the luminal surface of the end 22 and not present on the luminal surface of the mid-section 24. As mentioned, the reason for encapsulating only the ends 22 of stent-graft 10 is to increase its flexibility over a fully encapsulated stent, thereby allowing it to be bent into extreme curves without kinking. Most of the length of the device is covered by only a single layer of ePTFE which is extremely flexible and which does not strongly interact with the stent. Therefore, the flexibility of the single layer area is essentially that of the underlying stent device. FIG. 7 shows a fully encapsulated shape memory alloy stent bent in essentially as sharp a curve as possible. Note that the covering material is showing kinks or distortions 34 due to the inability of the covering material to move longitudinally relative to the stent structural members. FIG. 8 shows an identical shape memory alloy stent covered according to the current invention: only the extreme device ends are fully encapsulated. Note that the device is capable of being bent into a much sharper curve with little or no distortion of the covering or the underlying stent.

An additional advantage provided by the present invention is that the retraction force necessary to deploy the stent-graft 10 using a coaxial deployment system is drastically reduced in comparison to a fully encapsulated stent. This is due to the reduction in amount of covering material. Furthermore, by reducing the amount of covering material, the overall profile of the deployment system is reduced, allowing a wider range of applications. Another advantage enjoyed by the present invention is its ease of manufacture compared to stent-graft devices that place multiple stent rings over ePTFE tubing. Finally, an advantage over stent-grafts with a single layer of biocompatible material over the entire graft length is that because a strong bond is created in the encapsulated region, it is possible to transmit a pulling force from one end of the stent of the present invention to the other via the covering, making it possible to load into a sheath using pulling techniques. The preferred bare stent designs (chosen for flexibility and low profile) do not permit transmission of a pulling force in a longitudinal axial direction. This is because flexibility is increased and profile reduced by removing connections between longitudinally neighboring struts. The limited number of longitudinal connections has inadequate tensile strength to transmit the pulling force without failure. In the case of a true single layer covering (without use of adhesive, etc.) pulling on the covering causes the covering to slip off the stent. In the case of sutured single layer device pulling on the covering may cause the sutures holes to enlarge and even tear.

EXAMPLE 1

Two memotherm (shape memory alloy stent, product of Angiomed, Division of C. R. Bard, Inc.) biliary stents (S1 and S2), partially encapsulated according to the present invention, were loaded into a 10 French delivery system used for a standard covered biliary stent. The stents were 10 mm×60 mm. The pulling force necessary to load the stents (the force between the outer sheath and the stent) was measured as follows:

S1=6.3N

S2=3.5N

In comparison, the loading force for a fully encapsulated stent is approximately 50N. After loading the samples S1 and S2 into a pullback delivery system, both were deployed into a glass biliary duct model placed in a 37° C. water bath. All deployment went smoothly and no significant covering damage was observed. Thus, the partially encapsulated stents could be loaded employing a much-reduced force without being compromised structurally.

EXAMPLE 2

Three prototypes (P1, P2, and P3) were built using a Gamma 2 (Flexx) design memotherm stent, 12 mm×120 mm. These prototypes were partially encapsulated according to the present invention. More particularly, the abluminal surface of each stent was covered with a tubular ePTFE material, leaving the regions near the stent ends uncovered (to flare outward and anchor the device). The luminal surface near each end of the stent was covered by a 9.95 mm±0.05 mm ring of ePTFE material. The stents were then subjected to heat and pressure so that the overlapping ePTFE material on the luminal and abluminal surfaces was bonded together. The prototypes were then loaded into a 10 French delivery system and were deployed into a glass biliary duct model (45°, 25.4 mm radius) that was placed in a 37° C. water bath.

The prototypes were loaded according to the standard loading technique used for loading fully encapsulated stents. This loading technique consists of compressing the stents by pulling them through a funnel using specially designed hooks. When loading the fully encapsulated stent, a backing mandrel and core are used to create a uniform folded pattern in the compressed stent. In loading P1, no backing mandrel and core inside the stent were used, resulting in an unacceptable load due to the presence of folds. P2 was loaded using a backing mandrel (9.2 mm diameter) and a core (1.25 mm diameter), resulting in a successful load with no folds. P3 was loaded in the same manner as P2. Loading forces between the funnel and the stent and pulling forces between the stent and the outer sheath were measured as follows:

| Prototype | Peak Loading Force (N) | Peak Pulling Force (N) |
| --- | --- | --- |
| P1 | 12.5 | — |
| P2 | 27.5 | 12.9 |
| P3 | 18.5 | 14.8 |

The loading force and pulling force necessary to load and deploy the prototypes were much smaller than that necessary for a fully encapsulated stent. Thus making it possible to load and deploy the prototypes with either a manual pullback or a pistol handgrip deployment system.

Figure 4:
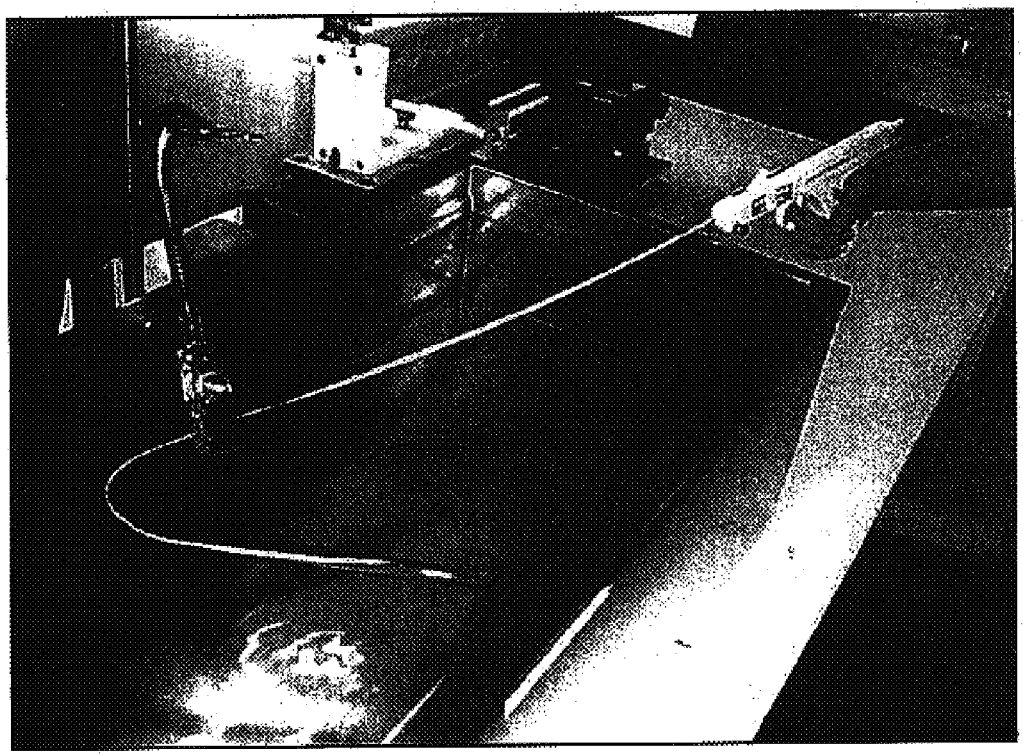
FIG. 4 is an overview picture of the deployment of the device of the present invention.
Figure 5:
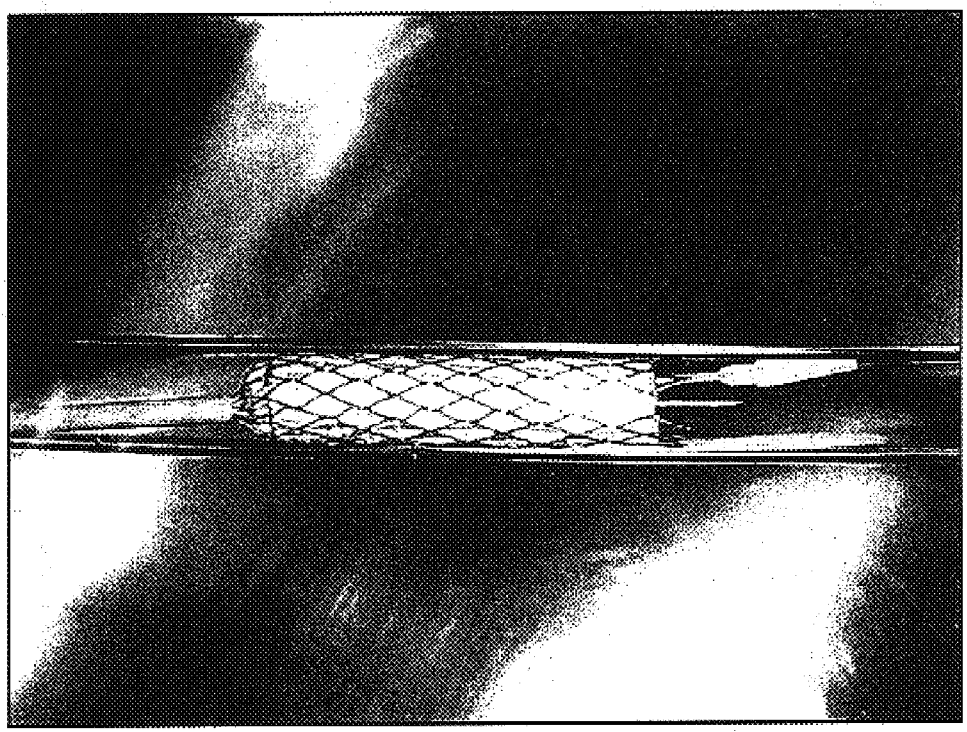
FIG. 5 is a close-up view of the device being partially deployed.
Figure 6:
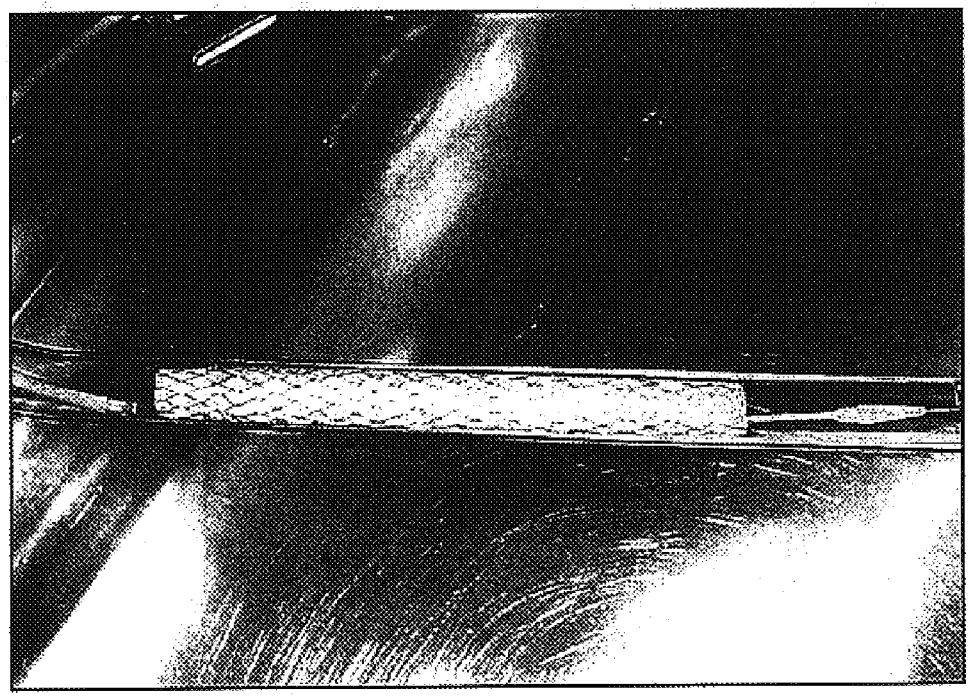
FIG. 6 is a close-up view of the device fully deployed.

In the case of a biliary stent an especially tortuous delivery path must be used. There are two main techniques for such delivery. If the stent is deliver transhepatically, it is inserted through percutaneous vasculature, through the bulk of the liver and down the hepatic duct where it must make a bend of around 45 degrees between the hepatic and the bile duct. If the stent is delivered endoscopically it enters the bile duct via the papilla and must pass through multiple bends, the most sever of which is about 90 degrees with a 10 mm radius. Clearly an extremely flexible stent is required. To further illustrate the deployment of the prototypes, FIGS. 4–6 have been provided. FIG. 4 shows an overview of the prototypes being deployed into a glass model of a bile duct using a pistol handgrip delivery system. Note the bend that the stent must navigate. FIG. 5 shows a close-up view of a prototype, as it is partially deployed from the sheath. FIG. 6 shows a close-up view of a fully deployed prototype.

The "Flexx" stent used in these experiments is a specially designed stent configured for the present invention. Stents of this type are cut from tubes of Nitinol shape memory alloy and then expanded on a mandrel. The size memory of the device is set on the expanded form. The device is then compressed to the approximate dimensions of the original tube for insertion into a patient. Once properly located in the patient, the device is released and can self-expand to the "memorized" expanded dimension. Although the entire device is a single unitary piece, as shown in FIG. 9 in its expanded state, this design conceptually comprises a plurality of zigzag ring stents 64 (stenting zones) joined by longitudinal joining points 62.

Figure 9:
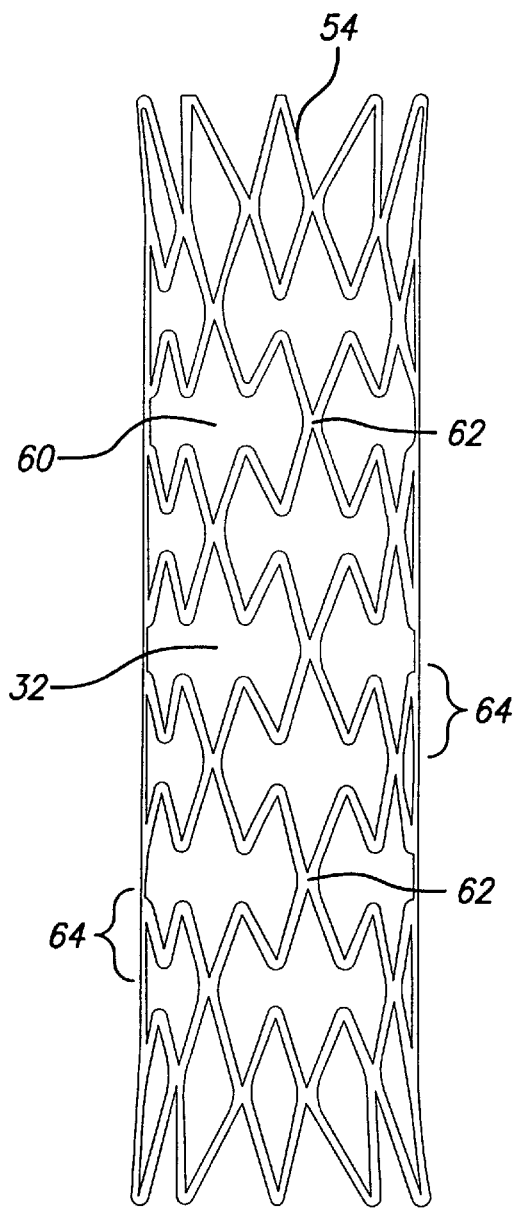
FIG. 9 shows an especially flexible stent design (the "Flexx" stent) preferred for use in the present invention; here the Flexx stent is shown in its expanded state.
Figure 10:
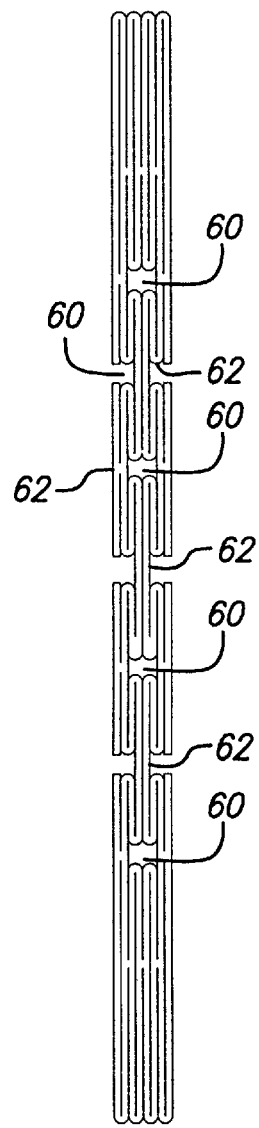
FIG. 10 shows the flexible stent of FIG. 9 after it has been compressed.

FIG. 10 shows the recompressed device to illustrate that each ring stent 64 is attached to each adjacent ring stent 64 by only a pair of joining points 64. Note the open regions 60 between the joining points 62. It will be apparent that such a structure affords considerable lateral flexibility to the entire compressed structure. If there were a larger number of joining points 64, lateral flexibility of the compressed device would be impeded. On the other hand, the very open structure of the expanded stent (FIG. 9) offers little resistance to tissue infiltration.

These two factors account for the unusual suitability of the Flexx design in the present invention. The use of a covering of ePTFE or other biocompatible material prevents tissue infiltration despite the very open nature of the Flexx design. The use of end encapsulation (as opposed to encapsulation over the entire length of the device) preserves most of the inherent flexibility of the design. The use of only a single layer of covering over much of the stent results in a low profile in the compressed configuration so that the device can be inserted through small bile ducts and other restricted vessels. The use of only a very limited number of joining points 64 provides the lateral flexibility required for insertion through tortuous bile ducts and other similarly twisted vessels.

Figure 11:
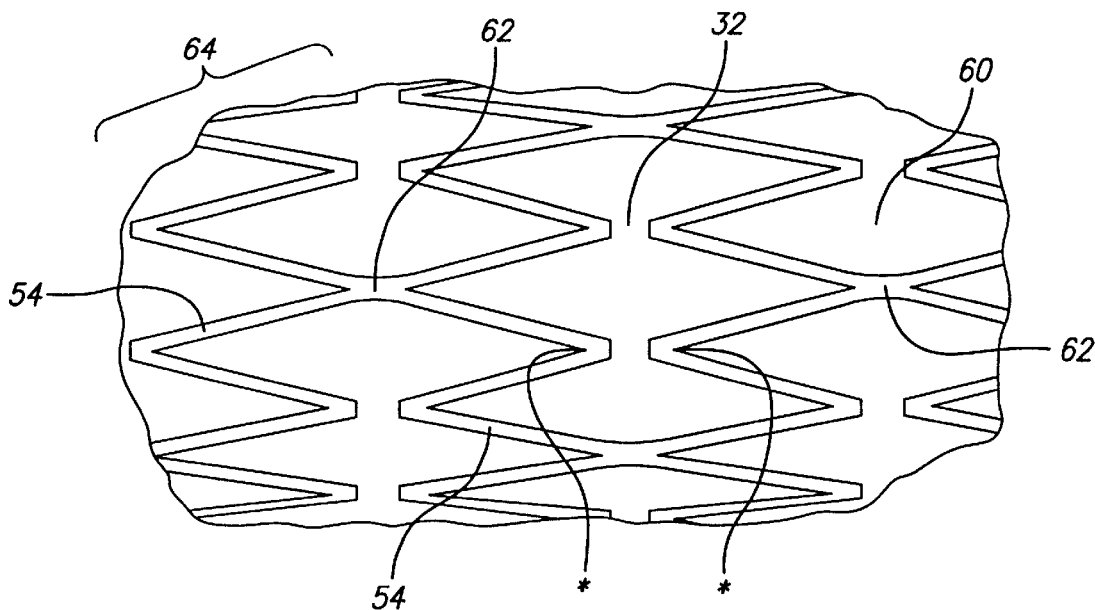
FIG. 11 shows a close-up of the strut structure of the expanded stent of FIG. 9.

FIG. 11 is a close-up of a portion of FIG. 9 and shows the adjacent ring stents 64 (stenting zones) and the joining points 62. Each ring stent 64 (stenting zone) is formed from a zigzag pattern of struts 54. These struts have the thickness of the Nitinol tube from which the device is laser cut with a width, in this embodiment, of about 0.2 mm. There is a joining point 62 between a given ring stent 64 and an adjacent ring stent 64 every third strut 54 with the joining points 62 alternating from the left-hand adjacent to the right hand adjacent ring stent 64 so that six struts 54 separate the joining points 64 between any two ring stents 64. Gaps 32 replace the joining points 62 where the intersections of zigzag struts are not joined.

Figure 12:
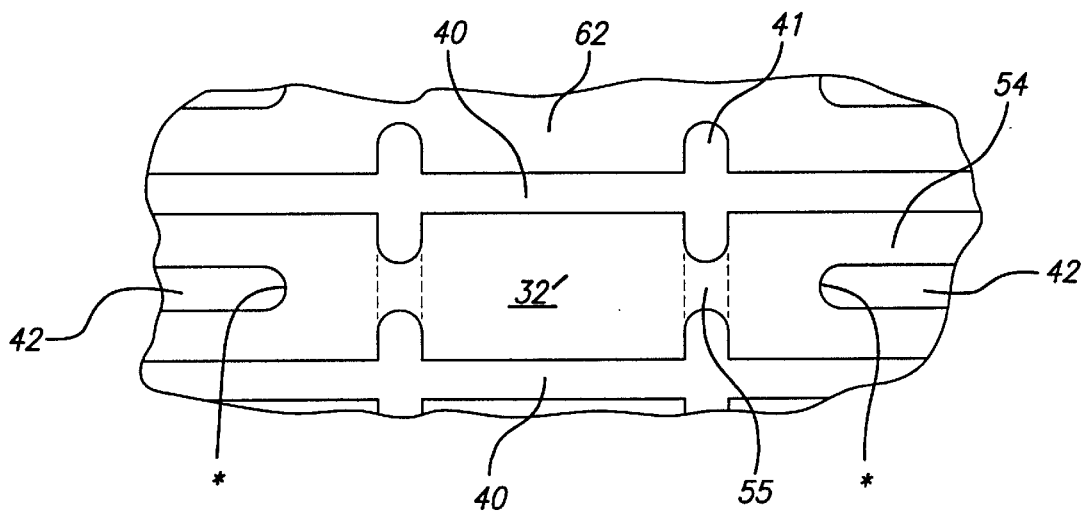
FIG. 12 shows a close-up view of the flexible stent design of FIG. 9 immediately after being cut from a metal tube and before being expanded into the form of FIG. 11.

FIG. 12 shows a close-up of the non-expanded cut structure of FIG. 10. Cuts 40, 41, and 42 are regions where the metal has been vaporized by a computer controlled cutting laser. The cut 40 between blind cuts 41 will expand to form the window 60. Cut 42 forms the intersection point * of the struts 54, which show portions of two ring stents 64. Partially cut regions 55 define a scrap piece of metal 32', which is removed following expansion to form the gaps 32. In the figure the partially shown region above the cut 40 and above the scrap piece 32' is the joining point 62. Because a structure with only two joining pieces 62 between adjacent stent rings 64 is too fragile to withstand expansion as from FIG. 12 to FIG. 11, the scrap pieces 32' act as reinforcing joining points for the radial expansion process. Following expansion the scrap pieces 32' are removed to form the gaps 32. This structure can then be deformed into the reduced diameter flexible structure shown in FIG. 10. It will be apparent that although this structure is described and pictured as having circumferential ring stents 64, the stents zones can also be arranged in a helical manner to achieve the objects of the improved design.

Having thus described a preferred embodiment of the covered stent with encapsulated ends, it will be apparent by those skilled in the art how certain advantages of the present invention have been achieved. It should also be appreciated that various modifications, adaptations, and alternative embodiments thereof may be made. For example, while

Flexx stent designs partially covered with ePTFE have been illustrated, it should be apparent that the inventive concepts described herein would be equally applicable to other types of stent designs and biocompatible covering materials. Moreover, the words used in this specification to describe the invention and its various embodiments are to be understood not only in the sense of their commonly defined meanings, but to include by special definition in this specification structure, material or acts beyond the scope of the commonly defined meanings. The definitions of the words or elements of the following claims are, therefore, defined in this specification to include not only the combination of elements which are literally set forth, but all equivalent structure, material or acts for performing substantially the same function in substantially the same way to obtain substantially the same result. The described embodiments are to be considered illustrative rather than restrictive. The invention is further defined by the following claims.

What is claimed as new and desired to be protected by Letters Patent of the United States is:

1. A flexible covered stent, comprising:
    a stent comprising a plurality of ring stents, each of said ring stents joined to an adjacent of said ring stents by at least one joining point, wherein said joining point is integral therewith;
    a first layer of biocompatible material, covering at least a portion of a first surface of said stent; and
    a second layer of biocompatible material, covering at least a portion of a second surface of said stent, said second layer having a length less than a length of said first layer, said second layer being positioned at a first end region of said stent, leaving at least a mid portion of said second surface of said stent uncovered, wherein said second layer is bonded to said first layer; wherein said length of said first layer is less than the longitudinal length of said stent such that at least one extremity of said stent is left uncovered by said first layer, wherein said uncovered extremity flares outward with respect to a longitudinal axis of the flexible covered stent upon expansion thereof.

2. The flexible covered stent according to claim 1, further comprising a third layer of biocompatible material, covering at least a portion of said second surface of said stent, said third layer having a length less than the length of said first layer, said third layer being positioned at a second end region of said stent, wherein said third layer is bonded to said first layer.

3. The flexible covered stent according to claim 1, wherein said first surface of said stent is an outer surface thereof and said second surface of said stent is an inner surface thereof.

4. The flexible covered stent according to claim 1, wherein at least one of said first and second layers of biocompatible material comprise expanded polytetrafluoroethylene.

5. The flexible covered stent according to claim 1, wherein said stent is formed from shape memory alloy.

6. The flexible covered stent according to claim 1, wherein said length of said first layer is less than the longitudinal length of said stent such that a first and second extremity of said stent are left uncovered by said first layer, wherein said uncovered extremities flare outward with respect to a longitudinal axis of the flexible covered stent upon expansion thereof.

7. The flexible covered stent according to claim 1, wherein the pulling force necessary to load the flexible covered stent into a delivery system is equal to or less than approximately 6.3 N.

* * * * *

UNITED STATES PATENT AND TRADEMARK OFFICE
CERTIFICATE OF CORRECTION

PATENT NO. : 6,740,115 B2  Page 1 of 1
APPLICATION NO. : 10/412138
DATED : May 25, 2004
INVENTOR(S) : Lombardi et al.

It is certified that error appears in the above-identified patent and that said Letters Patent is hereby corrected as shown below:

Column 8, Lines 5 and 9, "64" should be changed to --62--.

Signed and Sealed this

Twenty-eighth Day of November, 2006

JON W. DUDAS
*Director of the United States Patent and Trademark Office*